US005098657A

United States Patent [19]

Blackford et al.

[11] Patent Number: 5,098,657

[45] Date of Patent: Mar. 24, 1992

[54] APPARATUS FOR MEASURING IMPURITY CONCENTRATIONS IN A LIQUID

[75] Inventors: David B. Blackford, St. Paul; Frederic R. Quant, Shoreview; Thomas A. Kerrick, Forest Lake; Gilmore J. Sem, Lauderdale; Darrell D. Havir, Roseville, all of Minn.

[73] Assignee: TSI Incorporated, St. Paul, Minn.

[21] Appl. No.: 390,282

[22] Filed: Aug. 7, 1989

[51] Int. Cl.$^5$ ...................... G01N 15/12; G01N 15/14

[52] U.S. Cl. ...................................... 422/73; 422/110; 422/112; 422/115; 356/37; 356/335; 356/336, 356/337; 377/11; 377/12; 239/74; 137/115

[58] Field of Search .......................... 356/37, 335-337; 436/36; 422/73, 110, 112, 115; 377/11, 12; 239/74, 19; 137/115

[56] References Cited

U.S. PATENT DOCUMENTS

| | | | |
|---|---|---|---|
| 3,476,729 | 11/1969 | Smith et al. | 260/94.9 |
| 3,765,771 | 10/1973 | Shaw | 356/103 |
| 3,854,321 | 12/1974 | Dahneke | 73/28 |
| 3,984,296 | 10/1976 | Richards | 204/157.1 R |
| 4,173,415 | 11/1979 | Wyatt | 356/336 |
| 4,284,496 | 8/1981 | Newton | 209/3.3 |
| 4,361,400 | 11/1982 | Gray et al. | 356/23 |
| 4,449,816 | 5/1984 | Kohsaka et al. | 356/37 |
| 4,519,983 | 5/1985 | Espitalie et al. | 422/78 |
| 4,585,169 | 4/1986 | Kinsey | 239/75 |
| 4,761,074 | 8/1988 | Kohsaka et al. | 356/37 |
| 4,794,086 | 12/1988 | Kasper et al. | 436/36 |
| 4,853,618 | 8/1989 | Holley | 324/71.4 |

FOREIGN PATENT DOCUMENTS 266490 11/1965 Australia .

OTHER PUBLICATIONS

Blackford, D. B. et al., "A New Method for Measuring Nonvolatile Residue for Ultrapure solvents", J. of Environ. Sci. 30(4) 43-47, 1987.

Perry & Green, "Chemical Engineers Handbook", 6 ed. 1984, Chapter 22-26.

"Particle Characterization", David B. Blackford and Gary R. Simons, dated 22 Sep. 1986.

"Development of a New Continuous Monitor for Nonvolatile Solute in Ultrapure Water by Atomization", *The Journal of Environmental Sciences*, Kousaka, et al., Jul./Aug., 1987, pp. 39-42.

"Submicron Aerosol Characterization of Water by a Differential Mobility Particle Sizer", Kournikakis et al., *J. Aerosol Sci.*, vol. 19, No. 7, pp. 1425-1428, 1988.

"Development on an On-Line Method for Gauging the Total Weight of Foreign Materials in IC Pure Water", Takahasi et al., Automated Integrated Circuits Manufacturing, Proceeding of the 4th Symposium, Chicago 1988, Proceedings of the Electrochemical Society, pp. 155-162.

"A New Method for Measuring Nonvolatile Residue for Ultrapure Solvents", David B. Blackford et al., *The Journal of Environmental Sciences*, Jul./Aug. 1987, pp. 43-47.

"Aerosol Generation Method for Measuring Particles Suspended in Water-Detection of Particulate Impuri- (List continued on next page.)

*Primary Examiner*—David L. Lacey
*Assistant Examiner*—David Redding
*Attorney, Agent, or Firm*—Merchant, Gould, Smith, Edell, Welter & Schmidt

[57] ABSTRACT

An apparatus for measuring nonvolatile residue concentrations in liquid is disclosed. A plurality of fixed and adjustable flow restrictive elements are utilized and arranged in-line from a fluid supply source to provide a constant, pressure controlled flow of liquid to the measuring apparatus and allow for real-time measurements and optimal concentration detection. An atomizer atomizes the liquid into droplets which are dried to nonvolatile residue particles. The nonvolatile residue particle concentration is then determined utilizing an electrostatic aerosol detector. The invention further discloses apparatus for collecting a sample of nonvolatile residue for analysis and identification using a corona precipitator.

19 Claims, 9 Drawing Sheets

OTHER PUBLICATIONS ties in Ultrapure Water and Sizing of Fine Powders–", Niida et al., dated 11 Jan. 1988.

"Cleanliness Meter and its Application to Solvent Cleaning", Marsh, Fifth Annual Technical Meeting and Exhibit, Houston, Texas, Mar. 29–Apr. 1, 1966.

"Ultrapure Water Management in Semiconductor Factories Using a Total Evaporation Residue Meter", Tada et al., *Journal of Electronics Materials,* pp. 107–113, Jun. 1988.

"Development of a Continuous Monitor for Nonvolatile Impurity in Ultrapure Water and Solvents", Sato et al.

"Highpure Monitor", Nomura Micro Science, Pamphlet.

"Aerosol Technology in Hazard Evaluation", Mercer, American Industrial Hygien Association and U.S. Atomic Energy Commission, Production of Test Aerosols 9, pp. 336–367.

"Analysis of High Purity Chemicals: Examination and Improvement of the Residue after Evaporation Test for Solvents", Campbell et al., *Analytical Chemistry,* vol. 50, No. 7, Jun. 1978, pp. 963–964.

"Standard Test Method for Nonvolatile Matter in Volatile Solvents for Use in Paint, Varnish, Lacquer, and Related Products", American Society for Testing and Materials, D 1353, pp. 1–2.

"Book of SEMI Standards 1985", Semiconductor Equipment and Materials Institute, Incorporated, vol. 1, Chemicals Division, 1985.

"Laboratory Generation of Particulates With Emphasis on Submicron Aerosols", Benjamin Y. H. Liu, *Journal of the Air Pollution Control Association,* vol. 24, No. 12, pp. 1170–1172, Dec. 1974.

*Industrial Test News,* TSI Incorporated, vol. 2, Issue 1, p. 4, "Model 8110 Automated Filter Tester".

*TSI Journal of Particle Instrumentation,* vol. 3, No. 1, pp. 3–9, Jan.–Jun. 1988, "Generation and Maintenance of Process Gases with Extremely Low Particle Levels", Donald C. Grant.

APPARATUS FOR MEASURING IMPURITY CONCENTRATIONS IN A LIQUID

FIELD OF THE INVENTION

This invention relates to the measurement of nonvolatile residue in liquids, and more particularly to an improved constant pressure apparatus for delivering test liquid to an apparatus which measures nonvolatile residue in ultrapure liquids, for example, in the range of ten parts per million to less than one part per billion. The invention further relates to the collection of a sample of nonvolatile residue for further analysis and identification of the same.

BACKGROUND OF THE INVENTION

The current semiconductor manufacturing process for Very Large Scale Integrated circuits ("VLSI circuits") uses a single wafer of semiconductor material. In a VLSI circuit, many duplicate devices are simultaneously fabricated on the surface of the wafer. The fabrication process typically involves as many as sixty stages of chemically processing the wafer's surface. Between each stage of the processing, the chemical used in the previous stage must be thoroughly washed or cleansed from the wafer surface in a washing step. Ultrapure water is used in the washing step.

The volume of ultrapure water required to wash the chemicals from a single wafer for all stages of processing may total as much as 1000 liters. Any nonvolatile residue such as fine particles, microorganisms, and dissolved impurities have the potential to remain on the wafer surface after the water has evaporated. Since minute traces of residue material on a wafer surface can cause defects in the resulting semiconductor device, it is imperative to use ultrapure water of the highest quality/purity to limit possible defects. Therefore, instrumentation is required to monitor ultrapure water quality at nonvolatile residue quantities of a few parts per billion (hereafter referred to for convenience as "PPB").

An instrument capable of measurements of this nature is described in U.S. Pat. No. 4,761,074 issued to Kohsaka et al. Kohsaka et al discloses a method and apparatus for measuring impurity concentrations in a liquid. The apparatus includes an atomizer for atomizing the liquid by mixing it with clean air and generating droplets of a predetermined size distribution. An evaporator evaporates the fine droplets, thereby generating nonvolatile residue particles. A condensation nucleus counter (hereinafter referred to for convenience as "CNC") then counts the number of fine nonvolatile residue particles. A single processing unit measures the nonvolatile residue concentration of the liquid based on the sensitivity characteristic of the CNC, the distribution of the droplet size generated by the atomizer, and the number of particles counted by the CNC.

Another method and apparatus for measurement of impurities in liquids is disclosed in U.S. Pat. No. 4,794,086 issued to Kasper et al. The method includes dispersing the test liquid (i.e., the liquid to be measured for nonvolatile residue) into uniform droplets of a precisely known diameter in a gas stream using a vibrating orifice generator to disperse the liquid. The droplets are then evaporated leaving a nonvolatile residue particle having a known diameter. The static charge on the droplets and/or residue particles is then neutralized and the diameter of the residue particles is then measured. The residue concentration by volume within the liquid can then be calculated. The residue particles are sized by an optical particle counter, or alternatively a differential mobility size analyzer, in order to determine the impurity level.

Both of the systems described above involve dispersing the liquid to be measured for nonvolatile residue into droplets by using an atomization process. The droplets are then evaporated to leave a residue particle which is counted or sized. However, these systems do not allow for continuous control of the feed rate of the ultrapure liquids at an optimum flowrate as provided in the present invention.

Traditionally, a peristaltic pump with collapsible tubing has been used to feed the ultrapure water to a nozzle for atomization. A cylindrical ball bearing is used in conjunction with the pump and collapsible tubing to rotate and collapse the tubing to obtain the proper flowrate. Use of this type of pump system does not allow utilization of the industry standard materials for use with ultrapure water. Therefore, using this type of system introduces impurities into the ultrapure water through the pump system. Use of a syringe pump introduces the same type of contaminants as the use of the pump and collapsible tubing described above. Additionally, the above described systems do not provide a means for altering the operating range of the nonvolatile residue monitor.

The present invention addresses the above described problems associated with the apparatus and method of measuring nonvolatile residue in liquids. The apparatus operates in a more accurate, more controlled manner with an increased response time. The system preferably utilizes noncontaminating materials in its construction and includes means for controlling the liquid flow at a very low flowrate thereby eliminating the introduction of impurities into the ultrapure water. The system then utilizes means for accurately measuring the nonvolatile residue in the liquid. The system also uses a variable number of diffusion screens to alter the operating range of the nonvolatile residue monitor and allows collection of the residue for identification.

SUMMARY OF THE INVENTION

The present invention provides an improved method and apparatus for measuring low (i.e., PPB) concentrations in ultrapure water. A preferred embodiment constructed according to the principles of the present invention is especially suited for such measurements in a semiconductor fabrication wash water environment. The present invention utilizes feedback control to provide a steady controlled flow of test water to the atomizer portion of the test apparatus.

In a preferred embodiment of a measuring device constructed according to the principles of this invention, a plurality of flow restrictive elements are arranged in-line from a fluid supply source to an atomizer. An adjustable flow restriction element is connected in fluid communication with the fluid supply source. The adjustable flow restrictive element is located downstream of a first flow restrictive element, such adjustable element also being in fluid communication with a drain. The adjustable flow restrictive element is provided with information from pressure sensing means regarding the fluid pressure at a point between the first flow restrictive element and a second flow restrictive element. By adjusting the adjustable flow restrictive element properly, a constant pressure supply may be delivered to the second flow restrictive element and thus, to the atomizer from the water supply, thereby allowing for real time measurements and optimizing atomizer performance.

Further, a drain system is utilized which allows proper drainage of test water but does not allow contaminants to enter the test system. A means for collecting residue is also disclosed which allows for analysis and identification of the contaminant, thereby providing information as to the contaminant's source.

Therefore, according to one aspect of the invention, there is provided a measuring apparatus for measuring nonvolatile residue in a liquid including an atomizer for atomizing the liquid, means connected to the atomizer for drying the atomized liquid to nonvolatile residue particles, liquid delivery means for placing the liquid in fluid communication with the atomizer at a constant flowrate and means for measuring the nonvolatile residue. The measuring means includes a means for charging the particles and a means for measuring the charge.

Another aspect of the measuring apparatus includes liquid delivery means including a first fluid restrictive means, a pressure sensor, and a control valve wherein the sensor measures the pressure of the liquid at a point between the first fluid restrictive means and a second fluid restrictive means. The pressure sensor includes a pressure transducer to measure the pressure at a point between the first fluid restrictive means and the control valve and includes means for producing a first signal responsive to said measured pressure, an analog to digital converter connected to the transducer for producing a second signal responsive to the first signal, a microprocessor operatively connected to the analog to digital converter for comparing the second signal with a predetermined signal and providing an error signal, and means for adjusting the control valve, connected to the microprocessor and the control valve and responsive to the error signal, whereby the control valve maintains the pressure of the liquid supplied to the second fluid restrictive means at a predetermined value.

Yet another aspect of the present invention is a measuring apparatus for measuring nonvolatile residue in a liquid supply, of the type wherein an atomizer atomizes the liquid into droplets which are substantially dried to nonvolatile residue particles, the particles being counted utilizing condensation nucleus counting techniques, where the apparatus includes first fluid restrictive means in fluid communication with the liquid supply, for producing a flowrate, whereby a pressure variation is created, second fluid restrictive means, located downstream from said first fluid restrictive means, for restricting fluid flow to the atomizer, and variable fluid restriction control means, located between said first and second means and responsive to fluid pressure variations at a point between the first fluid restrictive means and the variable fluid restrictive control means, whereby variations of the pressure are automatically compensated for so as to provide constant fluid delivery to the atomizer.

One feature of the present invention is the recognition of the need to use noncontaminating materials. It is essential that particular care be taken in choosing the material for the wetable parts of the instrument. A wetable part is any surface that comes into contact with the ultrapure water prior to the point where measurement of nonvolatile residue is made. If a contaminating or other inappropriate wetable material is chosen, additional nonvolatile impurities are added to the ultrapure water and the impurity measurement is distorted. Therefore, preferably, materials chosen must not react with the water or other liquid used in the manufacturing process.

Another advantage of the present invention is that it provides an apparatus for controlling liquid flow at a very low flowrate which increases the accuracy to which the particles are atomized and therefore, measurement of impurities is done more accurately. Preferably, a series of sapphire orifices, a pressure sensor, and a motorized control valve responding to a control apparatus is utilized.

Yet another advantage of the present invention is the capability to measure impurities on-line or in a real-time manner. The present invention recognizes that it is highly desirable to make the impurity measurement on-line. That is, it is desirable to monitor impurities as the ultrapure water is supplied to the wafer manufacturing process. A continuous stream of ultrapure water is rapidly transported to the measurement device providing a rapid response time. This on-line measurement allows the semiconductor process engineer or monitor to be informed, typically in a matter of seconds, when water quality decays. This is a requirement for defect-free manufacture of wafers.

Still another feature of the device is the extension of the device's operating range. The operating range over which nonvolatile residue levels can be detected may be extended by the use of a variable number of diffusion screens. Diffusion screens block out particles of less than a predetermined diameter by capturing fine particles and allowing larger particles to penetrate the screen. Fine particles diffuse to the mesh of the screen by the forces of Brownian motion. Multiple screens capture particles with larger predetermined diameters and when placed upstream of a measuring device can thus be used to modify the efficiency of the device. By this means, the operating range of the nonvolatile residue monitor can be extended.

These and other advantages and features which characterize the present invention are pointed out with particularity in the claims annexed hereto and forming a further part hereof. However, for a better understanding of the invention, its advantages and objects obtained by its use, reference should be made to the drawings which form a further part hereof, and to the accompanying descriptive matter, in which there is illustrated and described a preferred embodiment of the present invention.

DESCRIPTION OF THE DRAWINGS

In the drawings, wherein like reference numerals represent like parts throughout the several views.

DETAILED DESCRIPTION OF THE PREFERRED EMBODIMENT

Figure 1:
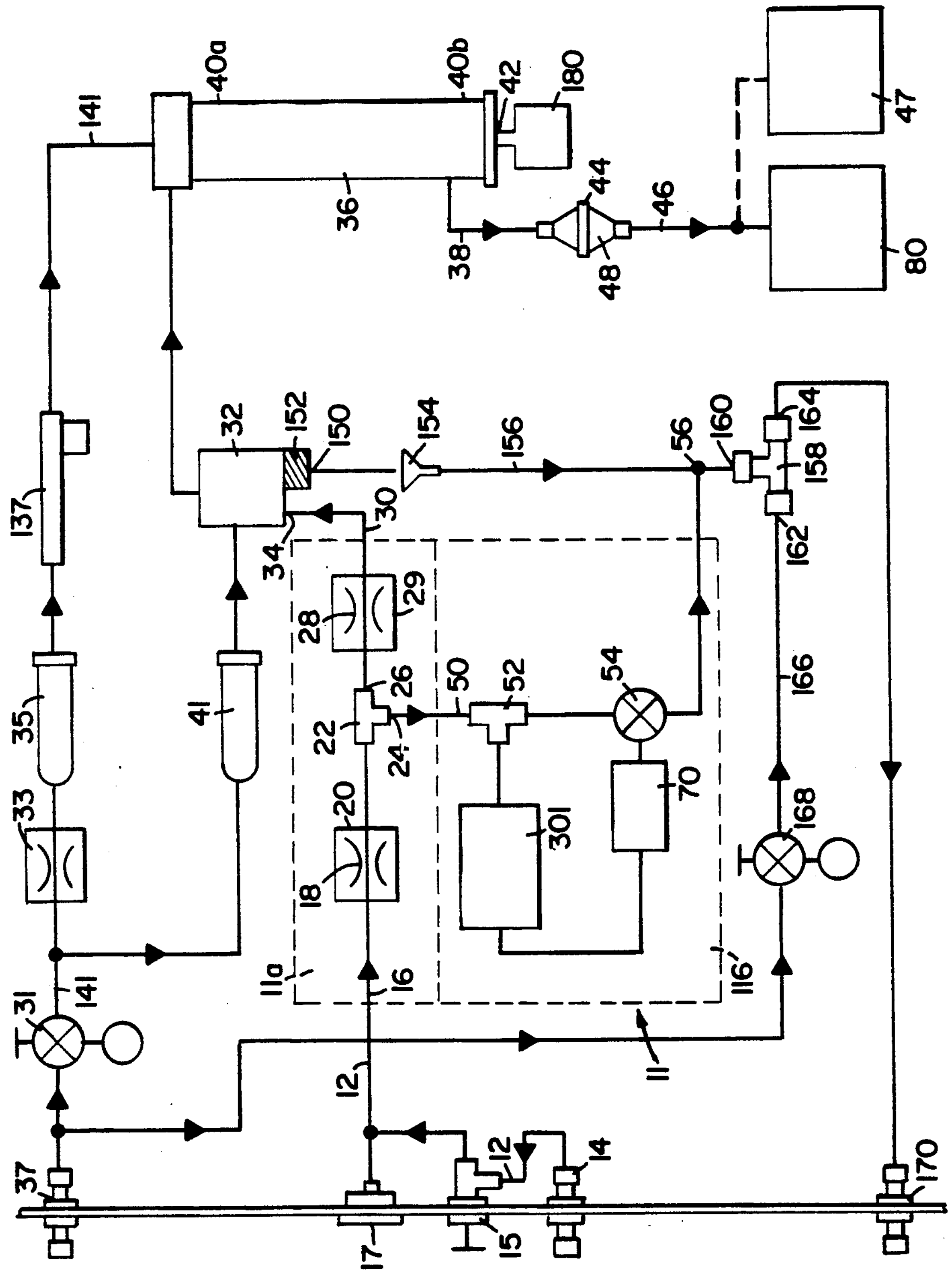
FIG. 1 is an unscaled diagrammatic illustration of the flow path of a test liquid containing residue through an apparatus for measuring impurity concentrations in a liquid according to the principles of the present invention.

The principles of this invention apply particularly well to its application in a semiconductor fabrication ultrapure wash water measurement apparatus. This invention provides a test fluid delivery system for automatically insuring that a controlled flowrate is delivered to the atomizer. The system is also preferably arranged and configured so as to provide the test fluid to the measurement device to allow for real time measurements. Although the invention is described in semiconductor fabrication applications, such application is typical of only one of innumerable types of applications in which the principles of the present invention can be employed. Further, although described with respect to ultrapure water, the present invention is similarly not limited.

In general, it is known that nonvolatile residue in ultrapure liquids can be measured by use of atomization, evaporation, and measurement and/or counting of the residue particles. An apparatus and method for measuring nonvolatile residue is disclosed in U.S. Pat. No. 4,794,086 to Kasper et al. In Kasper et al, liquid is led to a chamber where a vibrating orifice aerosol generator produces uniform droplets. The droplets are generated by controlling the break-up of the liquid. As the droplets are formed, they are introduced into an air jet which enters a chamber. The air jet acts to disperse the droplets and prevent coagulation. At this point, a larger volume of clean, dry air is added to the chamber to aid in the evaporation of liquid. As the droplets pass through the chamber, the liquid is evaporated to produce residue particles which are drawn into a tube and directed to a particle size analyzer. One type of particle size analyzer used is a light scattering particle spectrometer where the particles pass through incident light causing the light to scatter. The scattered light is detected by a collection optics system. The information from the optic system is then passed to a read out device.

Another apparatus and method similar to that described above is disclosed in U.S. Pat. No. 4,761,074 to Kohsaka et al. In this method, an atomizer is utilized to produce droplets of a predetermined size distribution. After the droplets are dried and reduced to residue, the residue is counted with a CNC device.

A CNC device can be used as a measuring means to detect the number of fine particles in the aerosol produced. Fine particles enter the CNC and pass through a cloud of vapor produced by heating a liquid such as butyl alcohol. Fine particles, in this case nonvolatile residue particles, act as sites upon which vapor can condense. Each individual residue particle effectively increases in size by virtue of the condensing vapor, until they are large enough to be counted by a conventional optical particle counter. This counter consists of a laser light source and focusing lenses. The aerosol, flowing perpendicularly, confronts the laser light and the particles of the aerosol scatter the laser light. Collecting lenses collect the scattered light at a photoelectric transducer which converts the light intensity to an electric signal. The signal of the photoelectric transducer is applied to a counter of the CNC. The counter counts the number of pulses from the photoelectric transducer and the counted data is transferred to a signal processing unit where the nonvolatile residue of the ultrapure water is measured based on the original size distribution of the droplet size of the atomizer, a limit of measurement of the particle size at the CNC, and the counted value of the counter unit.

As noted, a CNC device may be used to determine the concentration of nonvolatile residue particles in a liquid. Additionally, an electrostatic aerosol detector may be used to detect the concentration of nonvolatile residue. In the preferred embodiment of the invention, an electrical aerosol detector is used as a measuring means to detect the concentration of nonvolatile residue particles in the aerosol produced. The electrical aerosol detector includes an electrostatic charger of aerosol particles and a charged particle detector. The concentration of the nonvolatile residue particles is determined based on the charge measured. A charge is placed on the particles and the current on the charged particles is detected. The number of unipolar elementary charges applied to any particle is determined by the size of the particle. In order to facilitate a more thorough understanding of the operation of the nonvolatile residue monitor, discussion of the electrical aerosol detector will be deferred pending a more thorough discussion of the flow rate control means, atomizing and drying of the particles, drainage and diffusion filters.

Referring to the drawings, a possible configuration of an apparatus 10 for measuring residue in a test liquid is shown in the block flow diagram of FIG. 1. Ultrapure liquid is fed to the above described measuring devices. The flowrate must be accurate and constant to produce accurate results. A fitting 14 is cooperatively connected to a liquid supply line 12 in the preferred embodiment. A control valve 15 is connected to supply line 12 to better control the pressure at which the fluid enters the system. A pressure meter 17, connected downstream of valve 15 in supply line 12, aids in the monitoring of control valve 15. The supply line 12 is constructed of Teflon ® persfluoroalkoxy or "PFA" in the preferred embodiment. It should be understood that other materials which do not introduce contaminants at a permissible level may be used. The fitting 14 allows transport of the ultrapure liquid via flowrate control means 11, shown in dotted line in FIG. 1, to the measuring apparatus which detects impurities in the liquid. It should be understood that any other suitable means of transport or placement of flow rate control means in fluid communication with the ultrapure liquid (sample liquid) may be used.

Flow rate control means 11 is comprised of several flow restrictive elements, or orifices, and means for placing the sample liquid in fluid communication with the various elements 11*a* and a control system 11*b*. In the preferred embodiment, a first orifice or flow restrictive means 18 is located within tubing 16 downstream of fitting 14. In the preferred embodiment, the first orifice 18 is constructed of sapphire and has a diameter of 0.0142 inches. Further, in the preferred embodiment, the sapphire orifice 18 is mounted in a molded PFA housing (not shown) that is secured within a Teflon® PFA fitting 20. The first orifice 18 is sized and configured to produce a flowrate of approximately 50 milliliters per minute to a second orifice or flow restrictive means 28 in the preferred embodiment. PFA is used to provide a noncontaminating wetable surface. Those skilled in the art will recognize that other materials may be used which meet the specifications of this invention.

Still referring to FIG. 1, a second fitting 22 is cooperatively connected to tubing 16. The second fitting 22 includes an inlet, a first outlet 24 and a second outlet 26. The second outlet 26 allows the ultrapure liquid to flow to the second orifice 28. The second orifice 28 is sized and configured to allow a flowrate of approximately 0.5 milliliters per minute of the ultrapure liquid in the preferred embodiment. The second orifice 28 is cooperatively connected to tubing 30 and, in the preferred embodiment, the orifice 28 is constructed of sapphire with a diameter of 0.0028 inches. In the preferred embodiment, the sapphire orifice 28 is mounted in a molded PFA housing (not shown) that is secured with a Teflon® PFA fitting 29. The fitting 29 may be constructed so as to directly connect as an inlet port of atomizer 32 as next described.

In the preferred embodiment, an atomizer 32 is connected to the second orifice 28 such that the outer body of the orifice 28 is a fitting 29 which is operatively connected to the inside of the liquid entry port 34 of the atomizer 32. In the preferred embodiment, the fitting 29 of the orifice 28 screws into the atomizer 32. This arrangement places the liquid supply in fluid communication with atomizer 32.

The rate of the liquid to the atomizer 32 must be accurately controlled to control the size of the droplets formed by the atomizer 32. It is known in the art that by inherent design, an atomizer 32 demands a very low flowrate in order to perform correctly. The liquid flowrate required is approximately 0.5 milliliters per minute in the preferred embodiment. Fluctuations in the rate of liquid feed to the atomizer 32 result in fluctuations in the size range of the droplets produced. Both the variation of droplet size and droplet concentration have a catastrophic effect on the measurement of nonvolatile residue. Those skilled in the art will recognize that although various diameters and flow rates are described herein, such diameters and flow rates are illustrative only and will vary in accordance with the downstream requirements of the atomizer 32 among other design considerations.

In the preferred embodiment, the atomizer 32 is made from 316 stainless steel and all wetable parts are electropolished. As noted, the second orifice 28 provides a constant flowrate of approximately 0.5 milliliters per minute (given a fixed appropriate fluid pressure upstream of the second orifice), that required for correct atomization in the preferred embodiment. The atomizer 32 in the preferred embodiment is manufactured by TSI, Inc., of St. Paul, Minn., having a model designation Model 3076. The flowrate to the atomizer 32 is controlled by a feedback system which will next be briefly described. The cooperative interaction between atomizer 32 and the flowrate control system **11*b*** will then follow.

The flowrate control system **11*b* begins at outlet 24 of the second fitting 22. Ultrapure liquid is transported through first orifice 18 to second fitting 22 and through outlet 24 when the liquid passes through tubing 50. A pressure transducer or sensor 52 is cooperatively connected to tubing 50 and controls the position of a variable restrictive flow element 54 via control circuit 301 and motor 70. Variable restrictive flow element 54 is preferably a motorized control valve. The control system 11*b* is in communication with a drain at point 56. The ultrapure liquid passing through the pressure sensor 52 and restrictive flow element 54 is discharged to the drain at point 56**.

Figure 9:
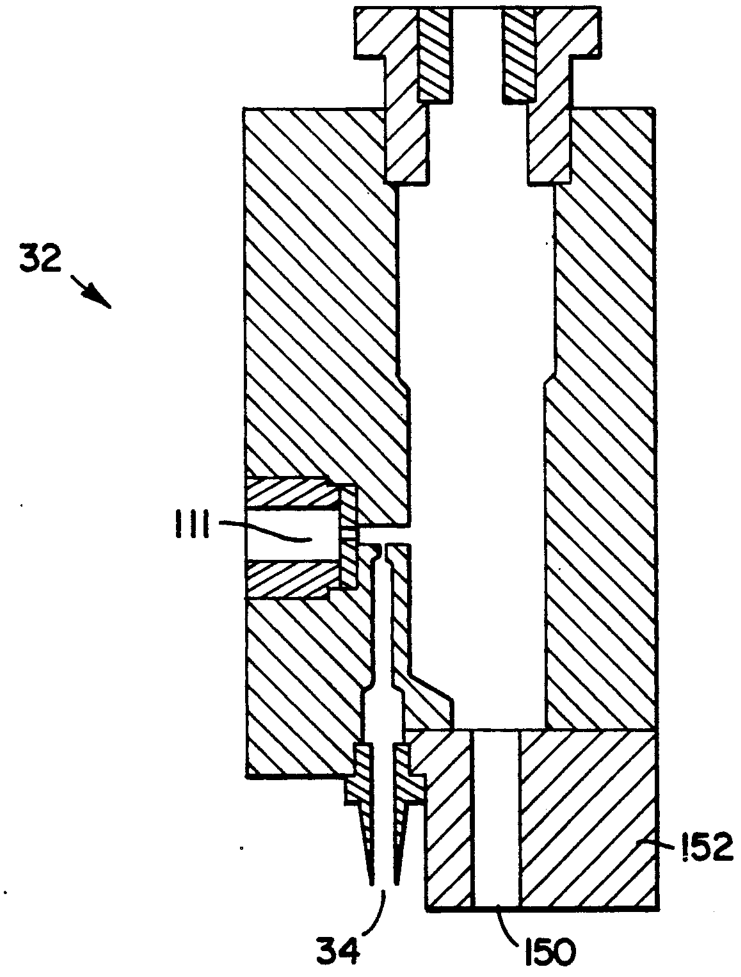
FIG. 9 is a preferred embodiment atomizer labeled block 32 in FIG. 1.

The atomizer 32 is supplied with compressed air or nitrogen to atomize the fluid. The gas is supplied by gas supply 37 connected to atomizer 32 and will be described in further detail below. The gas is introduced into atomizer 32 at venturi 111 (best seen in FIG. 9). Therefore, atomizer 32 utilizes a venturi effect whereby a negative pressure is created at the liquid entry port 34 to the atomizer 32. In the preferred embodiment, the pressure approximates −1.5 psi at the entry port 34. This considerable negative pressure at the entry port 34 aids in proper fluid flow to the atomizer 32 because the fluid is drawn into the atomizer 32.

The range of pressures measured by the pressure transducer 52 relative to atmospheric pressure are low and in the preferred embodiment, are in the range of 0.1–0.2 psi. Therefore, if the greater negative pressure created by the venturi effect in the atomizer 32 was not present, day to day variations in atmospheric pressure would affect the fluid flow to the atomizer 32 because the atmospheric pressure would affect the low pressures at the pressure sensor 52. The adjustments made by the flow control system 11 would therefore be affected by atmospheric pressure change so as to reduce the accuracy of the device.

A positive pressure is provided to the flow system 11 by a second orifice 28. This positive pressure allows fluid flow to the control system and drainage of excess water to the drainage system (to be described in further detail below). The interaction of these pressures and elements allows for a constant pressure drop across the second orifice 28 and therefore, the rate of liquid flow to the atomizer 32 remains constant.

Figure 2:
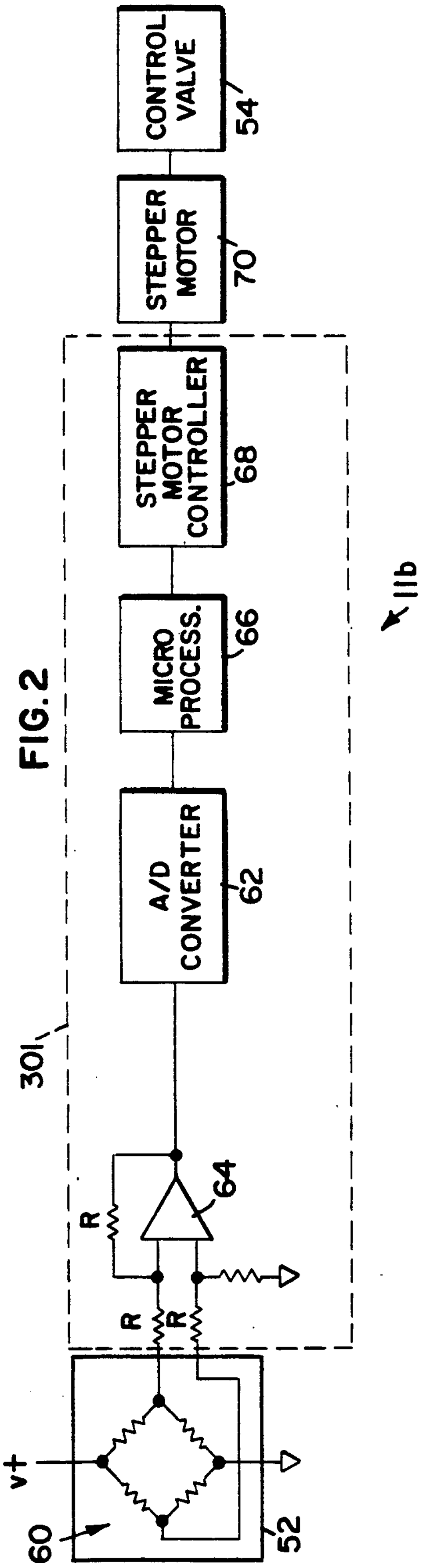
FIG. 2 is a block diagram illustrating functional elements of the pressure sensitive flow controller of the present invention.

Turning next to FIG. 2, the pressure sensor 52 acts as a pressure transducer, the output of which controls the positions of the motorized control valve 54. The block diagram of the functional elements of pressure sensor 52 is shown in FIG. 2. The pressure sensor 52 is a flow-through pressure sensing device including a four active element piezoresistive bridge 60. When ultrapure liquid under pressure flows through sensor 52, an output voltage proportional to the pressure is produced. In the preferred embodiment, pressure sensor 52 is manufactured by Honeywell Inc., Microswitch Division of Freeport, Ill. having a model designation of 156PC05 GW. An analog to digital (hereinafter referred to as "A/D") converter 62, of the successive approximation type, is connected to the piezoresistive bridge 60 via a differential amplifier 64.

A microprocessor 66 is connected to the A/D converter 62. A stepper motor controller 68 is connected to the microprocessor 66. In the preferred embodiment, the microprocessor is manufactured by Intel of Santa Clara, Calif. having a model designation 80C31. The stepper motor controller is manufactured by Hurst Manufacturing of Princeton, Ind. having a model designation 3206-001. A stepper motor 70 is operatively connected to the stepper motor controller 68. The control valve 54 is cooperatively connected to the shaft of the stepper motor 70.

Microprocessor 66 compares the converted digital signal provided by A/D converter 62 to a predetermined value stored in memory (not shown). Depending on whether the flowrate of the ultra pure water needs to be increased or decreased, a signal is generated by microprocessor 66 and transmitted to the stepper motor controller 68. When the stepper motor 70 receives a signal from the stepper motor controller 68, the stepper motor 70 opens or closes the valve 54 as required to maintain the accurate flowrate. Since the operation of stepper motors and their controllers are well known, they will not be described further herein.

Figure 5:
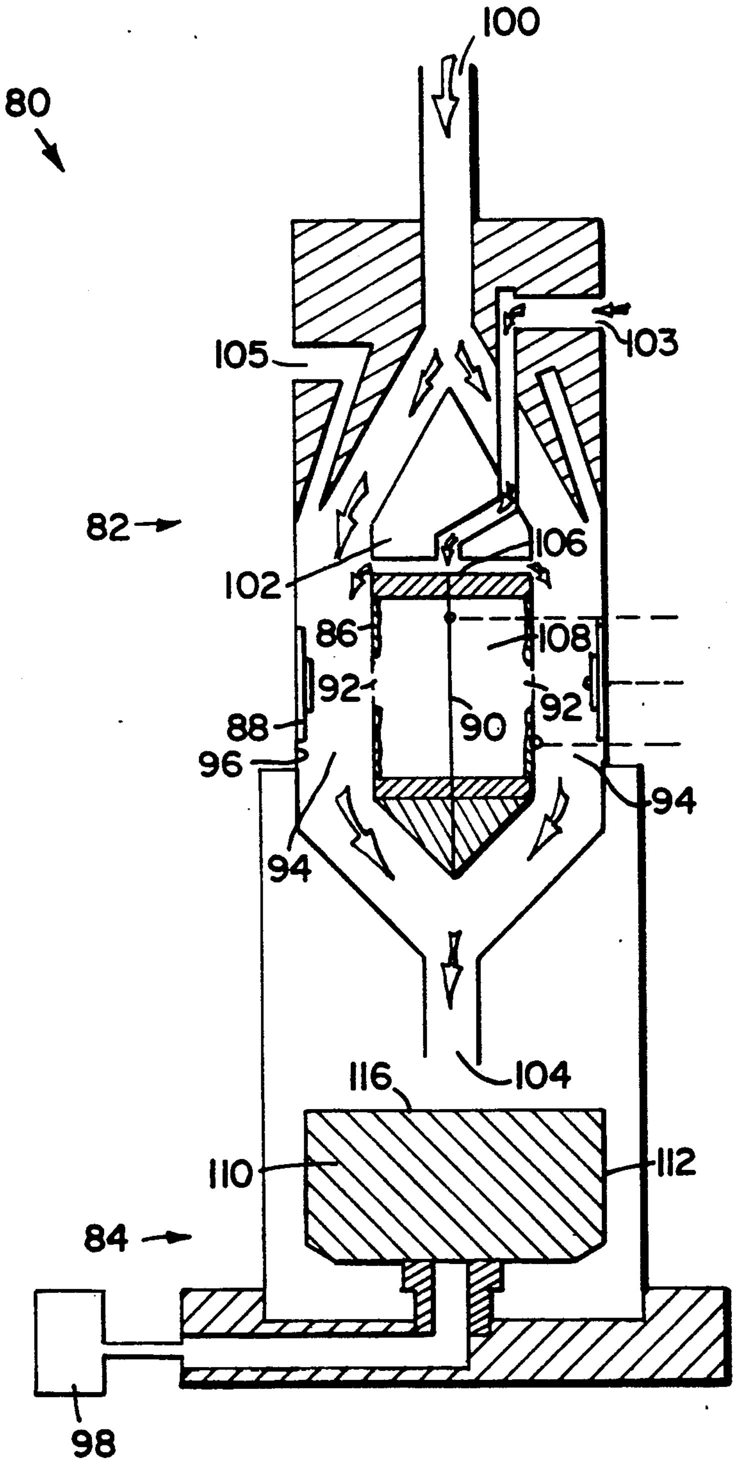
FIG. 5 is a schematic diagram of an optional electrostatic aerosol detector labeled block 80 in FIG. 1.
Figure 8:
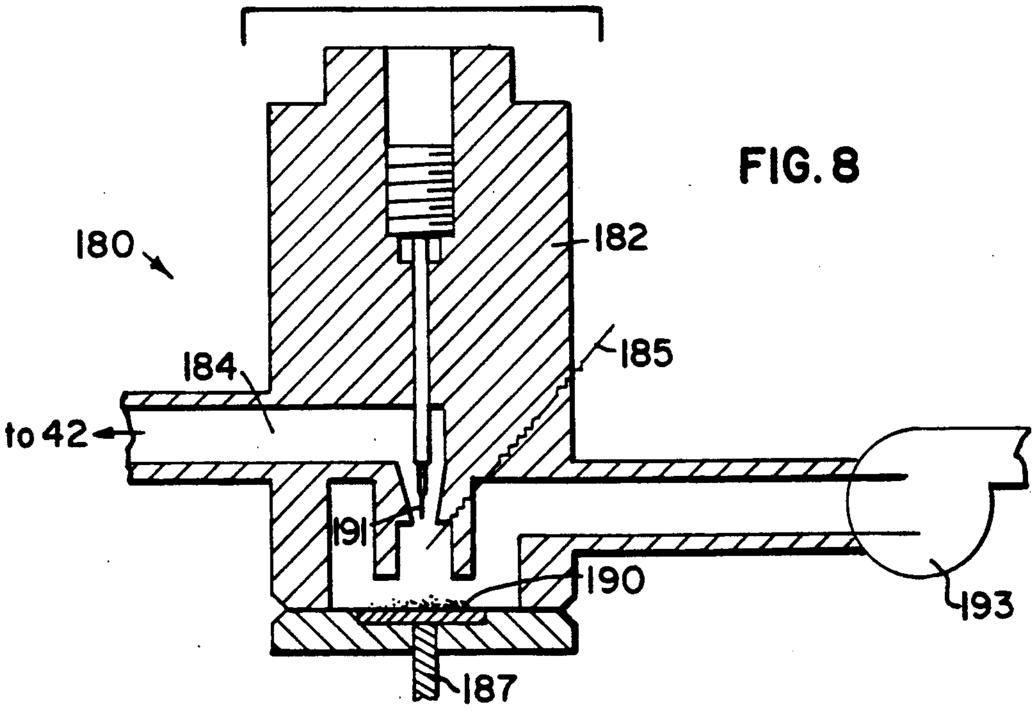
FIG. 8 is a schematic diagram of an optional corona precipitator labeled block 180 in FIG. 1.

While not specifically detailed in FIGS. 2, 5 and 8 it will be understood that the functional blocks, amplifiers and transducer portions are properly connected to appropriate bias and reference supplies so as to operate in their intended manner. Further, it will be understood that microprocessor 66, A/D convertor 62, and other appropriate functional blocks are connected to appropriate memory, buffer, and other peripheral devices and components so as to operate in their intended manner.

In summary, the pressure sensor 52 acts as a pressure tranducer, the output of which controls the position of the motorized control valve 54. In effect, the ultrapure liquid supply line pressure is dropped across the first orifice 18 and the valve 54. The pressure sensor 52. measures the ultrapure liquid pressure at fitting 22. As the pressure in the ultrapure liquid supply line 12 fluctuates due to intermittent or sustained demands for the pure liquids, the pressure sensor 52 will detect a fluctuating pressure, and open or close the motorized valve 54 accordingly. By this method, the pressure of the liquid presented to the second orifice 28 will always remain constant and therefore, the flow of the ultrapure liquid through the orifice 28 will also remain constant.

In the preferred embodiment, the physical distance between the second fitting 22 and the atomizer 32 is kept as short as possible. With this refinement, nonvolatile impurities flowing in the liquid supply line 30 are transported within 30 seconds to the atomizer 32 and are subsequently detected by the particle sensor within a fraction of a second. The nonvolatile residue monitor 10 can then be called a truly on-line system.

A gas supply 37 is connected in fluid communication with atomizer 32. The atomizer 32 receives the ultrapure liquid and with the compressed air or nitrogen from gas supply 37, atomizes the pure water, and generates a mist. The gas supply 37 is regulated by pressure regulator 31. The gas flows through filter 41 which is connected upstream from atomizer 32 to screen out impurities. The filter 41 is a pleated glass fiber high efficiency filter in the preferred embodiment. The mist created by atomizer 32 includes a large number of fine droplets having a predetermined size distribution. Large droplets, that is particles of several microns, impact the walls of the atomizer 32 and drain to the bottom of the atomizer device 32.

The large droplets, which drain to the bottom of the atomizer 32 must be removed from the atomizer 32. Because the system is a real time system with a large volume of water passing through the atomizer 32, adequate drainage is critical. The waste water must be removed continuously in a manner which allows water to drain but does not allow air to enter the atomizer 32 and contaminate the system. An outlet 150 is formed within the atomizer 32 to allow the water to drain. A material 152 is sized and configured to fit within the outlet 150 of the atomizer 32. In the preferred embodiment, the material 152 is natural sponge. However, it is to be understood that any other material may be used which meets the necessary specifications of the present invention. The material 152 must be configured to provide an air tight seal, but which allows water to drain out. Natural sponge provides these qualities. Natural sponge swells so that it fills the necessary portion of the atomizer 32 and provides an air tight seal while allowing the water to drip from the outlet 150. The present invention will not tolerate a pressure drop such as a drainage tube at this drainage point and the use of the natural sponge satisfies this requirement.

A collection means or funnel 154 is positioned in cooperation with the atomizer 32 to collect liquid draining from material 152 by means of outlet 150. A drain tube 156 is connected to collection means or funnel 154. A waste outlet 170 is connected to tube 156 to dispose of the liquid. Drain tube 156 is connected to a venturi 158. The venturi 158 includes an aperture 160 in the interior of the venturi throat, an entrance 162 and an exit 164.

The waste water drains from the material 152 and exits at outlet 150 into a funnel 154 where the water is then guided through drain tube 156. Compressed air or nitrogen from gas supply 37 is allowed to enter the venturi 158 at entrance 162 through pipe 166 which is regulated by pressure regulator 168. The compressed air or nitrogen flows through pipe 166 while being regulated by pressure regulator 168 to a predetermined flow. The gas enters the venturi 158 at entrance 162, passes through the venturi 158 and at the venturi throat carries the waste water, which enters at aperture 160, through the exit 164 of the venturi 158. The waste then drains to waste outlet 170 which is connected to a drain system.

After the atomizer 32 atomizes the liquid received at the correct flow rate, the mist is fed into a drying column 36 for measurement of the nonvolatile residue. In the preferred embodiment, heated filtered compressed air or nitrogen (hereafter referred to as "drying air") from gas supply 37 is forced by means of tubing 141 into the drying column 36 at 40*a* which evaporates the ultrapure water and leaves the nonvolatile residue particles in drying column 36. Pressure regulator 31 connected to tubing 141, shown in FIG. 1, regulates the flow of drying air to the drying column 36. Fixed orifice 33 connected to tubing 141 downstream of pressure regulator 31 further controls the flow of drying air. In the preferred embodiment, orifice 33 is a critical-type orifice. Use of a critical-type orifice allows for flow control without the use of other regulating means.

Filter 35, downstream of orifice 33, filters the drying air so that impurities are not introduced into the system. In the preferred embodiment, a pleated glass fiber, high efficiency filter is utilized. Heater 137 is connected to tubing 141 downstream of filter 35. Heater 137 heats the compressed drying air before it flows into drying column 36.

A sample of nonvolatile residue particles is drawn into tube 38 at the bottom 40*b* of the drying column 36. In the preferred embodiment, the particles are drawn into tube 38 by an internal pump of a CNC device 47 or a pump of an electrostatic aerosol detector 80 to be described later. Outlets 42, at the bottom of column 36, provide a means for exhaust of the particles not taken into the system at 38. A diffusion filter 44 is cooperatively connected to the tubing 38. Tubing 46 cooperatively connects a CNC device 47 or electrostatic aerosol detector 80 for calculating the impurity level of the liquid to diffusion filter 44 in two embodiments of the invention.

The detection sensitivity of a CNC 47 can be changed by adding the diffusion filter 44 immediately upstream of the CNC 47, as shown in the preferred embodiment in FIG. 1. The diffusion filter 44 removes ultrafine particles having sizes below a specified size. Ultrafine particles are impacted onto a fine mesh screen by forces of Brownian motion. Particles larger than the specified size are sufficiently uneffected by Brownian motion and are therefore passed through the diffusion filter 44 to the CNC device 47, while smaller particles are captured by the screen. Multiple screens capture particles with larger predetermined diameters and when placed upstream of a counting device can thus be used to modify the counting efficiency of the device. By this means, the operating range of the nonvolatile residue monitor can be extended.

Figure 3:
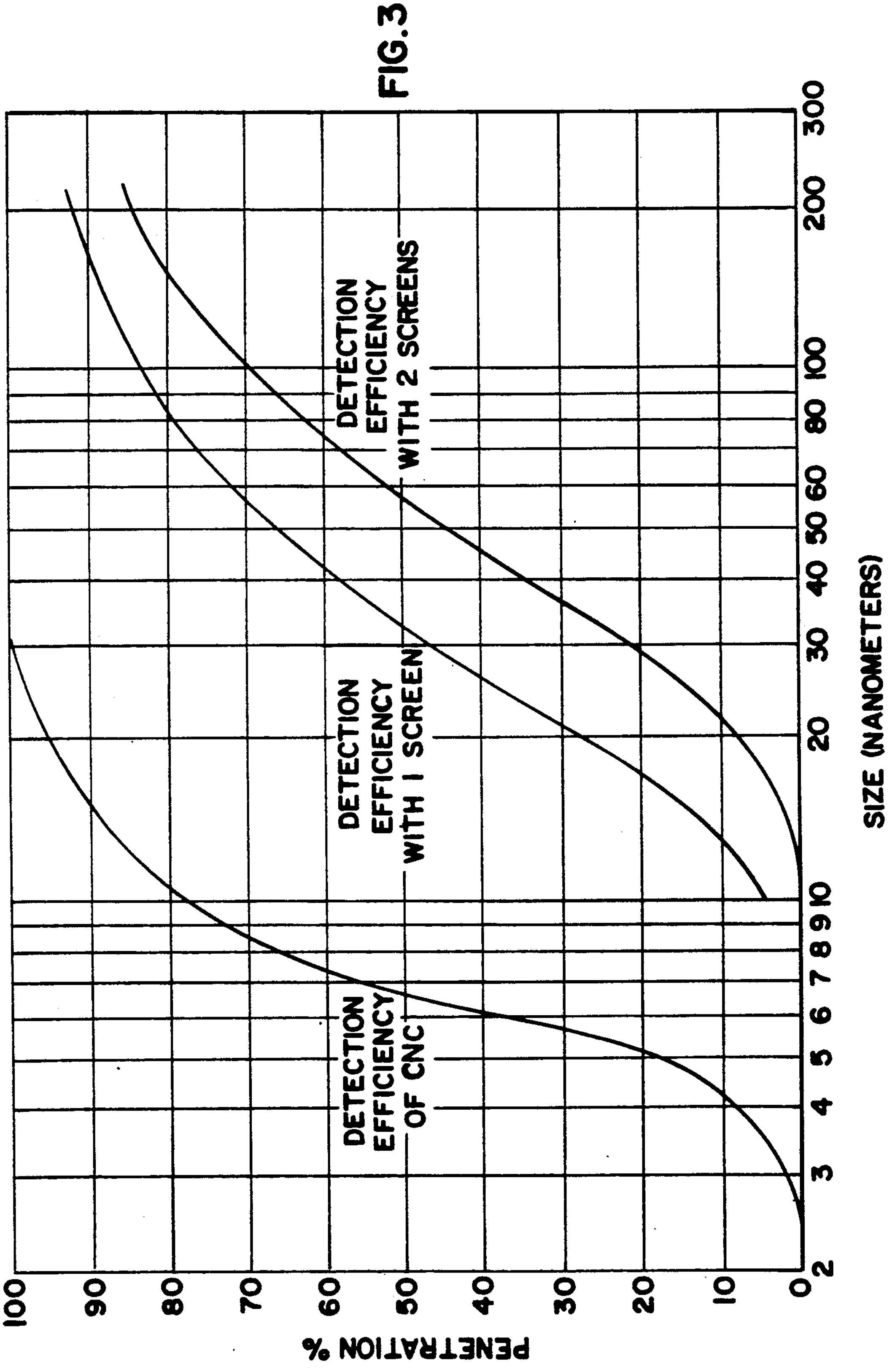
FIG. 3 is a graph illustrating the impurity detection efficiency of the present invention utilizing a condensation nucleus counter with a variable number of diffusion screens.

In the preferred embodiment, a diffusion filter housing 48 is utilized and cooperatively connected to tube 38. The housing 48 can contain several diffusion screens 44. The filters or screens 44 are made of stainless steel in the preferred embodiment and are of a fine mesh design. By varying the number of screens 44, it is possible to selectively remove particles less than a prescribed size. Only one or two screens 44 are required to provide the nonvolatile residue monitor with a wide operating range. For one embodiment of the invention, as shown in FIG. 3, the detection efficiency varies for a CNC device without a diffusion screen, a CNC with one diffusion screen and a CNC with two diffusion screens. The effect which the screen combinations have on the operating range of the nonvolatile residue monitor 10 utilizing a CNC device 47 is shown in FIG. 4.

Figure 4:
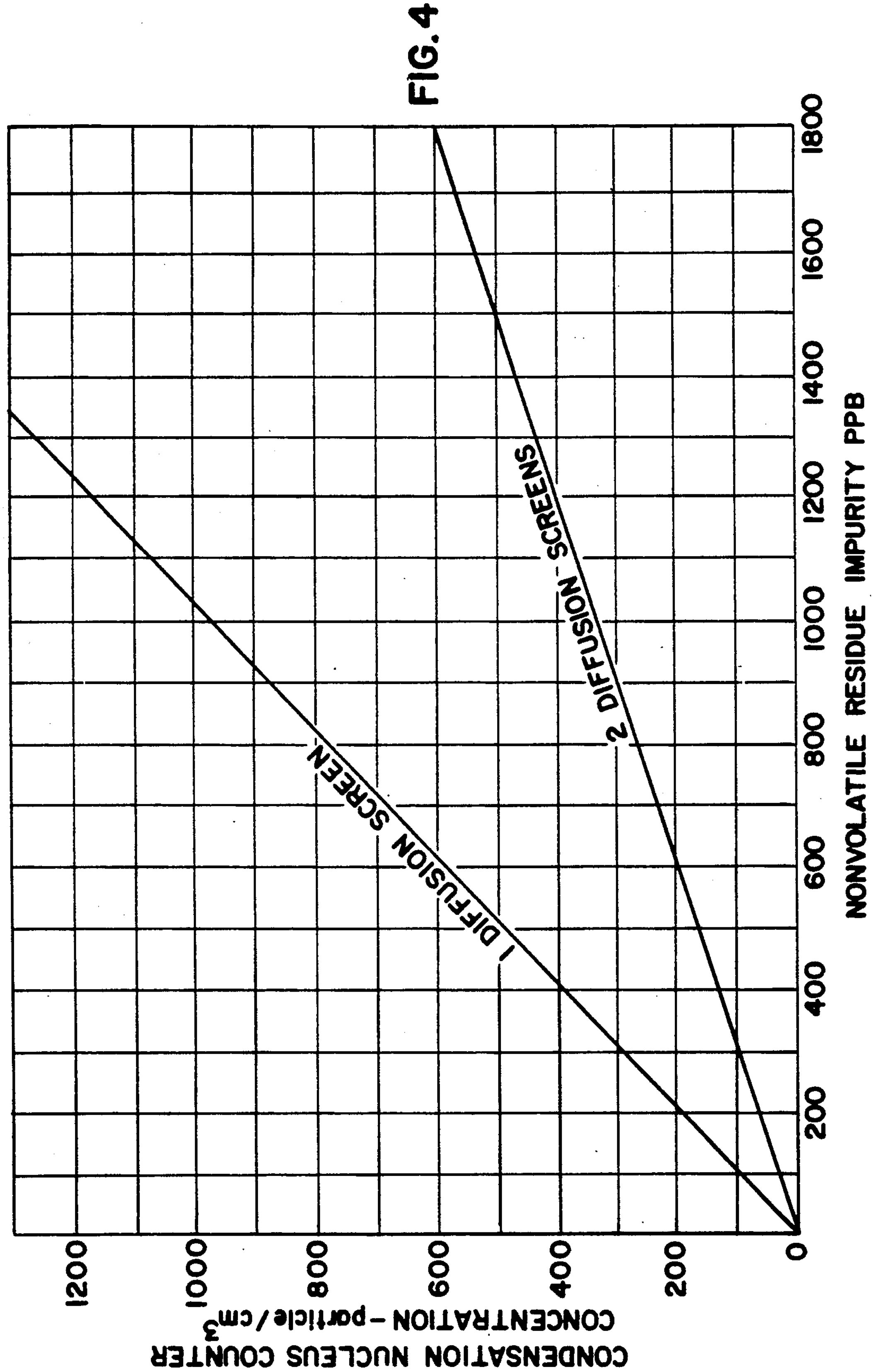
FIG. 4 is a graph illustrating the effect of using a variable number of diffusion screens in conjunction with a condensation nucleus counter in order to achieve varying calibration ranges.

FIG. 4 illustrates the direct relationship between the CNC count and the ultrapure liquid nonvolatile residue in parts per billion. Qualitatively measuring the nonvolatile residue count with the CNC and simultaneously measuring the quantitative nonvolatile residue count by the residue is described in U.S. Pat. No. 4,794,086 to Kasper et al. In effect, the Kasper technique has been used to quantify the nonvolatile residue monitor 10 without the need for the mathematical analysis together with its inherent assumptions.

The preferred embodiment of the invention utilizes an aerosol detector 80 to measure the nonvolatile residue in the ultrapure water in place of a CNC device. Tubing 46 cooperatively connects an aerosol detector 80 to the diffusion housing filter 48. The diffusion housing 48 and screens 44 may be utilized with the detector 80 to vary the operating range of this system 10 in a manner analogous to the effect of the screens 44 on a CNC device 47 as described above. One possible aerosol detector 80 is an Electrical Aerosol Detector (referred to hereinafter as "EAD") comprised of two primary components: (1) an electrostatic charger of aerosol particles 82 and (2) a charged-particle detector 84. The particles are charged and then the charge is measured. The concentration of nonvolatile residue is then determined based on the charge measured. There are several ways to place the necessary electrostatic charges on submicrometer airborne particles. In the preferred embodiment, diffusion charging is utilized. Diffusion charging takes place when airborne particles are exposed to airborne unipolar ions. In order to facilitate a more thorough understanding of the operation of the EAD 80, discussion of the same will be deferred pending a more thorough discussion of corona discharge, charger portion 82 and electrometer 84.

FIG. 5 illustrates one possible design for an aerosol particle charger 82. The charger 82, sometimes called a diffusion charger, is in the form of two concentric metal cylinders 86, 88 with a fine (25-mm diameter in the preferred embodiment) tungsten wire 90 connected to cylinder 86 and located along the axis of the cylinders 86, 88. Inner cylinder 86 includes a corona discharge region 108. An annular space 94 separates the two cylinders 86, 88. The inner cylinder 86 has a screen opening 92 for current flow and a screen 106 to prevent particles from being drawn into the cylinder 86. The EAD 80 includes a top inlet 100 to annular space 94 and an exit 104. An upper cone 102 is also included and connected to inner cylinder 86 to aid in fluid flow. The EAD also includes inlets 103 and 105 for sheath air which may be introduced into the apparatus.

A positive high voltage on the wire 90 produces a corona discharge. It is known in the art that charge density tends to be relatively high on sharp points. The electric field at points above a charged surface is proportional to the charge density so that the electric field may reach high values near sharp points. A corona discharge is produced if the conducting object has a high potential and is surrounded by air. The positively charged conductor attracts negative ions from the surrounding air. If the electric field at a sharp point is great enough, the ions will be accelerated and will collide with air molecules. This produces a great number of additional ions and, therefore, the air is made more conducting.

In operation, the positive ions produced by the corona discharge migrate toward the inner cylinder 86 where they either deposit on the inner surface of the cylinder 86 or flow radially through the screen opening 92 on the inner cylinder 86. Once outside of the screen opening 92, the ions migrate radially through an annular space 94 toward the outer cylinder wall 96. The inner cylinder 86 carries a positive voltage relative to the electrically-grounded outer cylinder 88. The level of the voltage on the inner cylinder 86 regulates the current flow through the screen opening 92. Within the annular space 94, the ions collide with the axially-flowing aerosol particles, resulting in the electrostatic charging of the particles.

A downstream pump 98, shown in FIG. 5, draws aerosol into the charger portion of the EAD 80. The top inlet 100 introduces aerosol particles into the charger 82. An upper cone 102 uniformly distributes the aerosol into the annular space 94 surrounding the inner cylinder 86 of the charger 82 as shown by the arrows in FIG. 5. The inlet 100 has negligible impaction loss of particles up to 5 μm. The aerosol flows through the annular space 94 between the inner cylinder 86 and the outer cylinder 88 in a laminar fashion due to the design of the EAD 80. While the aerosol moves through the annular space 94, the radially-moving ions charge the particles. The charged aerosol continues to flow in space 94, finally exiting the charger portion of the EAD 80 at exit 104.

In the annular space 94, the aerosol may be surrounded by two streams of particle-free sheath air. The inner sheath air, which is introduced at sheath air inlet 103 by standard industry equipment (not shown), flows adjacent to the inner-cylinder screen 106. This air flow prevents the aerosol particles from being drawn into the corona discharge region 108 inside the inner cylinder 86. If particles enter the corona discharge region 108, they acquire a higher electrical charge, resulting in a broad charge distribution on the particles and unacceptably high deposition of particles on the cylinder walls.

The outer sheath air, introduced at outer sheath inlet 105 by standard methods and equipment (not shown), displaces the aerosol stream away from the outer cylinder 88. The introduction of outer sheath air prevents charged particles from precipitating onto the walls of the outer cylinder 88. Both the introduction of the inner and outer sheath air streams also provide a more uniform velocity profile for the aerosol flow in the charging region, resulting in more uniform charge on particles of a given size.

Figure 6:
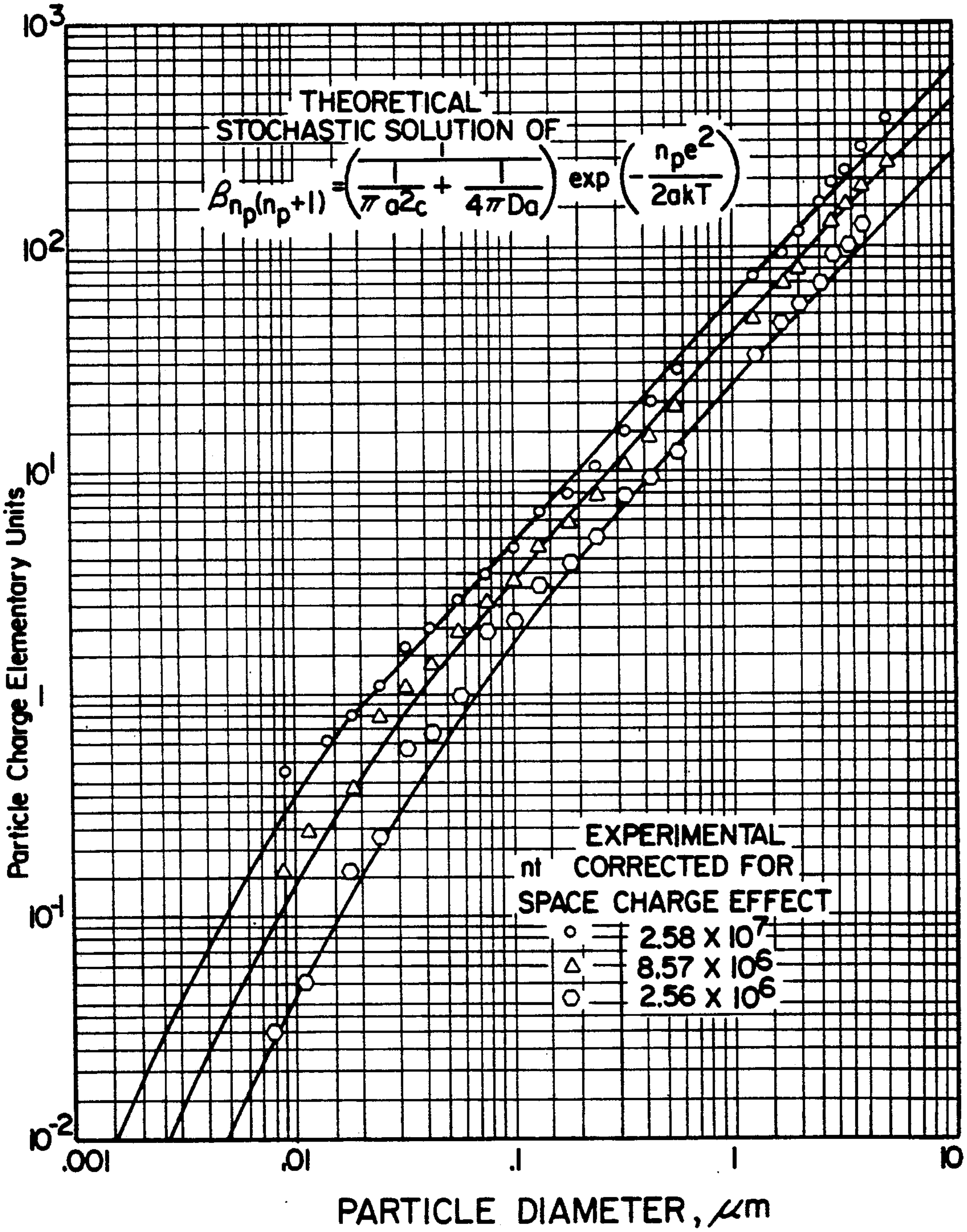
FIG. 6 is a graph illustrating the charge levels of particles as a function of particle diameter.

The number of unipolar elementary charges applied to any particle is determined by the size of the particle ($d_p$), its exposure time to the airborne unipolar ions (t), and the unipolar ion concentration (n). For any given particle size, the number of unipolar elementary charges it will acquire is a function of the mathematical product of (n) and (t). FIG. 6 shows the charge levels as a function of particle diameter for three values of (nt).

FIG. 6 illustrates that larger particles carry a larger charge than small particles for a given (nt) value. When dried particles in the nonvolatile fine residue aerosol have a mean diameter of 0.1 μm, the charged nonvolatile fine residue aerosol particles carry about 10 times more current than when the mean diameter is 0.01 μm. This is true because the concentration of nonvolatile fine residue aerosol particles is constant regardless of the nonvolatile residue concentration in the ultrapure liquid. For size distributions with constant shape and constant concentration, the fraction of ultrafine particles detected by an electrostatic aerosol detector depends on the mean diameter of the distribution.

The second portion of the EAD 80 is an electrostatic charge detector 84, also called an aerosol electrometer. The aerosol electrometer detects the current on the charged particles. The electrical current, $I_i$, carried by particles within a narrow size range with particle concentration, $N_i$, and carrying $n_i$ elementary charges each, is expressed by the equation:

$$I_i = qeN_in_i$$

where $e = 1.6\times10^{-19}$ coulomb = the elementary unit of charge and q = the aerosol flowrate. Therefore, the total current, I, carried by particles of all sizes is:

$$I = (qe)\sum_{i=1}^{\infty} N_in_i.$$

A possible configuration of an electrometer is shown schematically in FIG. 5. The aerosol electrometer 84 includes a high-efficiency particle filter 110 having an inlet 116 within an electrically conductive housing 112 that connects to the input of a high-sensitivity operational amplifier (not shown). Those skilled in the art will recognize that sensitive parts of the aerosol electrometer 84 must be carefully shielded to permit the detection of low concentrations of aerosols.

Therefore, the EAD 80 operates by charging the particles in the aerosol in charger section 82 and detecting the particles in electrometer 84. As the aerosol containing the charged particles exits the charger 80 and enters the filter 110 at inlet 116, particles deposit on the filter 110 surfaces. The electrostatic charges on the particles "drain off" the particles and the filter 110, passing into the inlet of the operational amplifier. The filter 110 may be made of an electrical insulator in the preferred embodiment. Because like-polarity charges repel each other, a current is created on an electrically conductive path to the operational amplifier. The amplifier then converts the low current levels into a voltage that is detectable by ordinary means.

Figure 7:
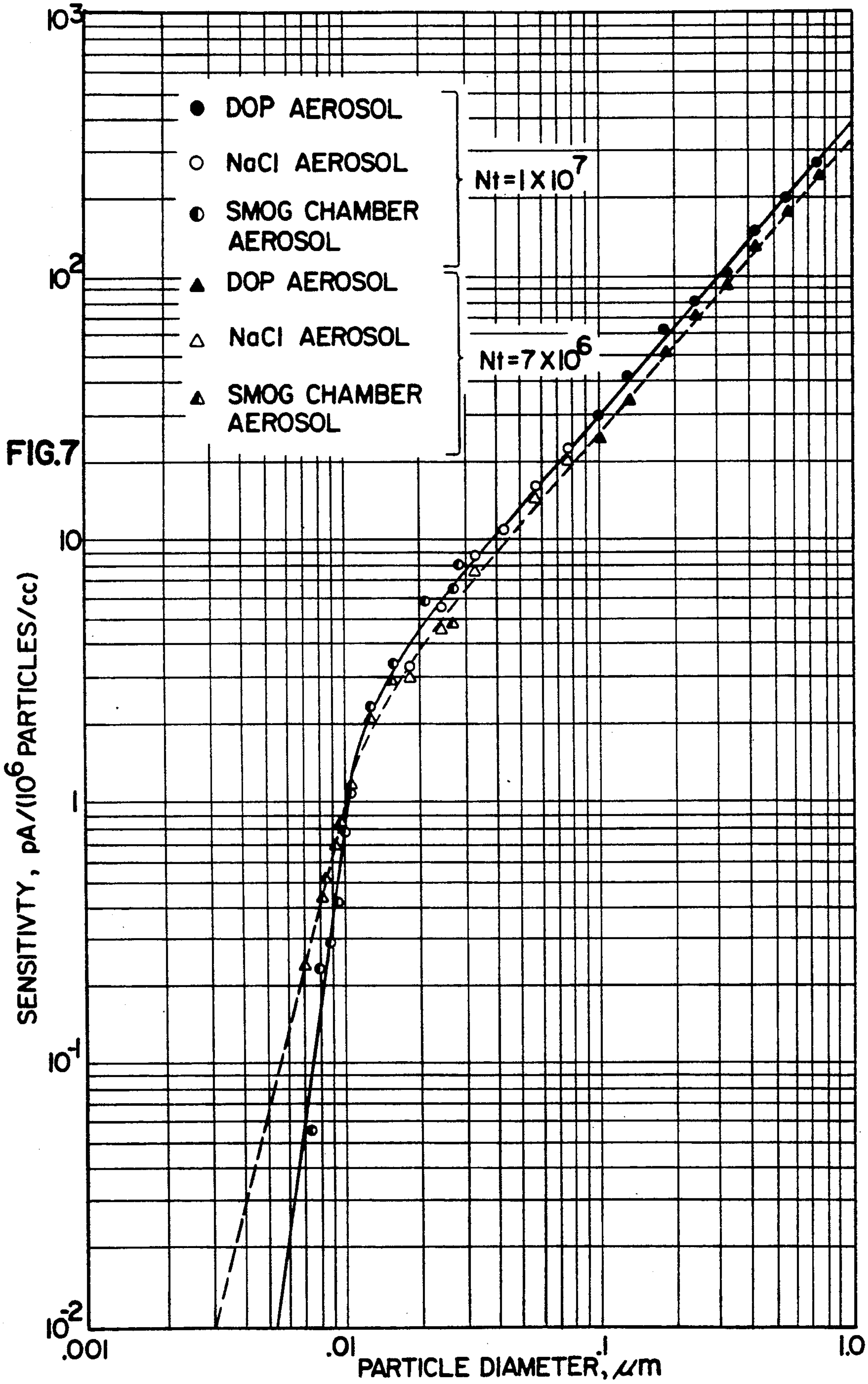
FIG. 7 is a graph illustrating the sensitivity of an electrical aerosol detector as a function of particle size.

The lower detection limit of the nonvolatile residue measuring instrument is directly proportional to the minimum electrical current detectable by the aerosol electrometer 84. Existing aerosol electrometers are capable of detecting charged aerosol currents of $2\times10^{-16}$ amperes. As calculated from experimental data shown in FIG. 7, as disclosed by B. Y. H. Liu and K. W. Lee in "An Aerosol Generator of High Stability," *American Industrial Hygiene Association Journal*, 36(12): 861-865 (1975), this corresponds to a particle concentration of 200 particles per cubic centimeter for 0.01-μm particles or 10 particles per cubic centimeter for 0.1-μm particles. FIG. 7 illustrates the sensitivity of the EAD as a function of residue particle size.

If ultrapure liquids have a nonvolatile residue concentration of 1 part per million by volume and the atomizer produces droplets with mean diameters of about 1 μm, the dried nonvolatile residue aerosol mean diameter will be 10 nanometers. Much of the particle distribution is detectable by an EAD. For example, if ultrapure liquids have a nonvolatile residue concentration of ppbv (parts per billion by volume) and the atomizer 32 produces droplets with mean diameters of about 1 μm, the dried nonvolatile residue aerosol mean diameter will be 1 nanometer. Only a small portion of the large-particle tail of the distribution will be detectable by the EAD 80. Reduced sensitivity to smaller particles makes it possible for the EAD 80 to be used to measure the concentration of nonvolatile residue in ultrapure liquids.

Another aspect of the invention allows for collection of residue for the determination of the identity of the residue and, thus, the identity of the source of the contamination. A corona precipitator may be optionally utilized to collect the residue. The corona precipitator 180 (best seen in FIGS. 1 and 8) is cooperatively connected to the drying column 36 at exhaust outlets 42 described above.

Referring now to FIG. 8, the corona precipitator 180 is shown. The corona precipitator 180 comprises a block 182 having a chamber 184 and a microscope stub or substrate 187 including surface 190 connected to the block 182. The corona precipitator further includes means to create a corona precipitation region 185 and a precipitator needle 191 connected to and positioned within the precipitation region 185. A vacuum pump 193 is connected to the corona precipitator 180.

The block 182 is constructed of TEFLON® in the preferred embodiment, an excellent electrical insulator. The chamber 184 of the corona precipitator 180 is configured as small as possible. The depth of the chamber 184 is configured to allow time for the particles to become charged and precipitate onto an electron microscope stub or substrate 187, but small enough to maintain a stable corona current with reasonable voltages. It is known in the art that creation of a corona precipitation region 185 at a high voltage power allows operation at a constant corona current. It is important to carefully control power to the precipitator needle 191, thus ensuring a constant corona current. A constant corona current ensures a constant particle collection efficiency. The vacuum pump 193 draws the residue through the corona precipitator 180. The combination of flowing air provided to the system by vacuum pump 193 and the electric field generated by the precipitator needle 191 carries the nonvolatile residue particles to the surface 190 of the electron microscope substrate 187. The high adhesive forces created between the particles and the surface 190 causes the particles to stick firmly to the surface. The electron microscope substrate 187 may be removed and placed within an electron microscope. By this means, the particles may be identified by elemental comparison and the cause of the contamination in the ultrapure water may be analyzed.

In order to identify the elemental composition of the nonvolatile residue deposited on the surface of the substrate 187, the electron microscope must be equipped with an energy dispersible analysis system. When the electron beam strikes the nonvolatile residue particles, characteristic x-rays are emitted. The energy dispersive x-ray analysis system can characterize this x-ray emission and report elemental composition. Through this elemental analysis, the potential cause of the nonvolatile residue contamination in the ultrapure water may be identified. An analysis of this nature is useful in locating the contamination source within the ultrapure water production system, such that corrective measures can be quickly taken to eliminate the source of the contamination.

While a particular embodiment of the invention has been described with respect to its application in delivering a constant fluid supply to an atomizer in a semiconductor fabrication wash water measurement apparatus, it will be understood by those skilled in the art that the invention is not limited to such application or embodiment or to the particular components disclosed and described herein.

It will be appreciated by those skilled in the art that other configurations that embody the principles of this invention and other applications other than as described herein can be configured within the spirit and the intent of this invention. The configuration described herein is provided only as an example of one embodiment that incorporates and practices the principles of this invention. Other modifications and alterations well within the knowledge of those skilled in the art are to be included within the broad scope of the appended claims.

What is claimed is:

1. An apparatus for measuring residue particles in a fluid, comprising:

(a) an atomizer for atomizing a fluid;

(b) means cooperatively connected to said atomizer for drying atomized fluid to produce residue particles;

(c) delivery means, cooperatively connected to said atomizer, for placing the fluid in fluid communication with said atomizer at a constant flowrate, said delivery means including a first orifice, a second orifice, a pressure sensor and control valve means, wherein said sensor is constructed and arranged so as to measure the fluid pressure between said first orifice and said control valve means and generate a first signal indicative thereof, and wherein said control valve means is positioned and arranged so as to respond to said generated signal and maintain the liquid pressure at a predetermined value to said second orifice, and (d) means for counting the residue particles connected in flow communication with said drying means.

2. The apparatus of claim 1 wherein said pressure sensor includes:

(a) a pressure transducer constructed so as to measure the fluid pressure between said first orifice and said control valve means and for producing said first signal;

(b) an analog to digital converter, cooperatively connected to said transducer, constructed so as to produce a second signal responsive to said first signal;

(c) a microprocessor operatively connected to said analog to digital converter constructed so as to compare said second signal with a predetermined value and producing an error signal; and (d) means for adjusting said control valve means, said adjusting means operatively connected to said microprocessor and said control valve means, said adjusting means being responsive to said error signal, whereby said control valve means maintains the measured fluid pressure at a predetermined value.

3. The apparatus of claim 1 further including at least one diffusion screen, said diffusion screen operatively connected to said counting means and constructed so as to alter the operating range of the apparatus for measuring residue.

4. An apparatus for measuring nonvolatile residue particles in a liquid, comprising:

(a) an atomizer for atomizing liquid and producing droplets;

(b) an evaporator in flow communication with said atomizer for evaporating the droplets into residue particles;

(c) a condensation nucleus counter in flow communication with said evaporator for counting the residue particles; and (d) means for controlling the flow rate of the liquid to the atomizer in flow communication with said atomizer, including a first and second orifice in fluid communication with one another, a pressure sensor and a control valve means, a processing means connected to said pressure sensor and said control valve means, said control valve means in fluid communication between said first and second orifices so as to respond to signals generated from said processing means, wherein said sensor is positioned and arranged to measure the liquid pressure between said first orifice and said second orifice and the pressure measurements are provided to said processing means, and wherein variations of the pressure are automatically compensated for by said processing means so as to provide constant liquid delivery to the atomizer, said control valve means in flow communication with a fluid disposal means for disposing fluid, wherein when the pressure is above a predetermined value, said processing means provides a signal to said control valve means which opens allowing more fluid to flow into said fluid disposal means and when the pressure is below a predetermined value, said processing means provides a signal to said control valve means which closes allowing less fluid to flow into said disposal means.

5. A nonvolatile residue particle analyzer in combination with an atomizer and a liquid supply, said atomizer in flow communication with said liquid supply which is constructed to atomize the liquid in said supply into droplets which are subsequently dried to nonvolatile residue particles in an evaporator which is in flow communication with said atomizer, the residue particles being counted by a counting means connected to said evaporator, said combination further comprising:

(a) first fluid restrictive means, in fluid communication with the liquid supply, for producing an approximate flow rate;

(b) second fluid restrictive means, arranged and configured in fluid communication with said first fluid restrictive means, for restricting fluid flow to the atomizer; and (c) variable fluid restriction control means, located in fluid communication between said first and second fluid restrictive means and responsive to variations in the liquid pressure between said first and second fluid restrictive means, for compensating for changes in the pressure variations, whereby variations of the pressure are automatically compensated for so as to provide constant fluid delivery to the atomizer.

6. A fluid delivery apparatus in combination with a liquid supply and an atomizer constructed so as to atomize the liquid in the supply into droplets, said combination further comprising:

(a) first fluid restrictive means, in fluid communication with the liquid supply, for producing an approximate flowrate;

(b) second fluid restrictive means, arranged and configured in fluid communication with said first fluid restriction means, for restricting fluid flow to the atomizer; and (c) variable fluid restriction control means in fluid communication between said first and second fluid restrictive means and responsive to fluctuations in fluid pressure between said first fluid restrictive means and said second fluid restrictive means, for automatically compensating for fluctuations in the fluid pressure, wherein variations in the fluid pressure are automatically compensated for so as to provide constant fluid delivery to the atomizer.

7. The apparatus of claim 6, wherein said first and second restrictive means include orifices.

8. The apparatus of claim 7, wherein said first and second fluid restrictive means are made of sapphire.

9. The apparatus of claim 6; wherein said variable restrictive control means includes a pressure sensor and a control valve means wherein said sensor is constructed so as to measure said fluid pressure between said first fluid restrictive means and said second fluid restrictive means and generate a first signal indicative thereof, and wherein said control valve means responds to said generated signal to maintain said fluid pressure at a predetermined value.

10. An apparatus for measuring the nonvolatile residue concentration of a fluid, comprising:

(a) an atomizer for mixing the fluid with clean air or nitrogen to produce droplets having a constant size distribution;

(b) an evaporator connected to said atomizer for evaporating the droplets leaving residue particles;

(c) first fluid restrictive means for producing an approximate flowrate of the fluid;

(d) second fluid restrictive means, located in fluid communication downstream from said first fluid restrictive means, for restricting fluid flow to the atomizer;

(e) variable fluid restriction control means, located in fluid communication between said first and second fluid restrictive means and responsive to pressure between said first fluid restrictive means and said second fluid restrictive means and for compensating for changes in the pressure; whereby variations of the pressure are automatically compensated for so as to provide constant fluid delivery to the atomizer; and (f) measuring means, connected in fluid communication with said evaporator, for measuring the concentration of the detectable nonvolatile residue particles.

11. The apparatus of claim 10 wherein said first and second fluid restrictive means include orifices.

12. The apparatus of claim 11, wherein said first and second fluid restrictive means are made of sapphire.

13. The apparatus of claim 10, wherein said variable restrictive control means includes a pressure sensor and a control valve means, wherein said sensor is positioned and arranged so as to measure the pressure between said first fluid restrictive means and said second fluid restrictive means and generate a first signal indicative thereof, so that said control valve means responds to said generated signal to maintain said fluid pressure at a predetermined value.

14. The apparatus of claim 10 wherein said means for measuring the concentration of residue particles includes a condensation nucleus counter.

15. The apparatus of claim 10, further including means for collecting the residue particles for identification, said collecting means in fluid communication with said measuring means.

16. The apparatus of claim 15, wherein said means for collecting the residue particles is a corona precipitator.

17. The apparatus of claim 10, further including a means for draining the non-atomized fluid from said atomizer and said variable fluid control restriction means.

18. The apparatus of claim 17, wherein said means for draining includes a material which provides an air tight seal while allowing fluid to drain, a means for collecting the fluid and a means for disposing of the fluid.

19. The apparatus of claim 18, wherein said material is a natural sponge.

* * * * *